United States Patent
Izumi et al.

(10) Patent No.: US 7,449,134 B2
(45) Date of Patent: Nov. 11, 2008

(54) DAST TWIN CRYSTAL, PROCESS FOR PRODUCING THE SAME, AND USE THEREOF

(75) Inventors: Atsushi Izumi, Ibaraki (JP); Yuta Ochiai, Ibaraki (JP); Shinsuke Umegaki, Kawasaki (JP); Tomo Iwamura, Yokohama (JP); Makoto Suzuki, Tokyo (JP); Hidetaka Sakurai, Tokyo (JP); Shinji Yamaguchi, Tokyo (JP)

(73) Assignees: Daiichi Pure Chemicals Co., Ltd., Tokyo (JP); Daiichi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 11/490,643

(22) Filed: Jul. 21, 2006

(65) Prior Publication Data

US 2007/0023739 A1   Feb. 1, 2007

Related U.S. Application Data

(63) Continuation of application No. PCT/JP2005/000511, filed on Jan. 18, 2005.

(30) Foreign Application Priority Data

Jan. 23, 2004   (JP)   ............... 2004-015399

(51) Int. Cl.
*F21V 9/00* (2006.01)
*B01D 9/02* (2006.01)
*C30B 28/04* (2006.01)
*C30B 29/54* (2006.01)

(52) U.S. Cl. .............. 252/582; 252/584; 117/3; 117/16; 117/902

(58) Field of Classification Search ................ 252/582, 252/584; 117/3, 16, 902
See application file for complete search history.

(56) References Cited

U.S. PATENT DOCUMENTS 5,617,104 A * 4/1997 Das ..................... 343/700 MS

FOREIGN PATENT DOCUMENTS

| JP | 3007972 B1 | 9/2000 |
| JP | 2001-247400 A | 9/2001 |
| JP | 2002-29899 A | 1/2002 |
| WO | WO 96/37639 | 11/1996 |

OTHER PUBLICATIONS

CAPLUS 1995: 817067.*
CAPLUS 2000: 496893.*
CAPLUS 2003: 561773.*
International Search Report for International Application No. PT/JP2005/000511 dated Mar. 25, 2005.

* cited by examiner

*Primary Examiner*—Shean C Wu
(74) *Attorney, Agent, or Firm*—Sonnenschein Nath & Rosenthal LLP

(57) ABSTRACT

Noble crystal of 4-dimethylamino-4-stilbazolium tosylate (DAST) useful as an electro-optical element. A DAST crystal having a size effective for use as an electro-optical element is provided by a twin crystal of DAST. The twin crystal of DAST can be obtained according to a seed crystallization method or a slope crystal growing method.

8 Claims, 3 Drawing Sheets

(a)

(b)

FIG. 5
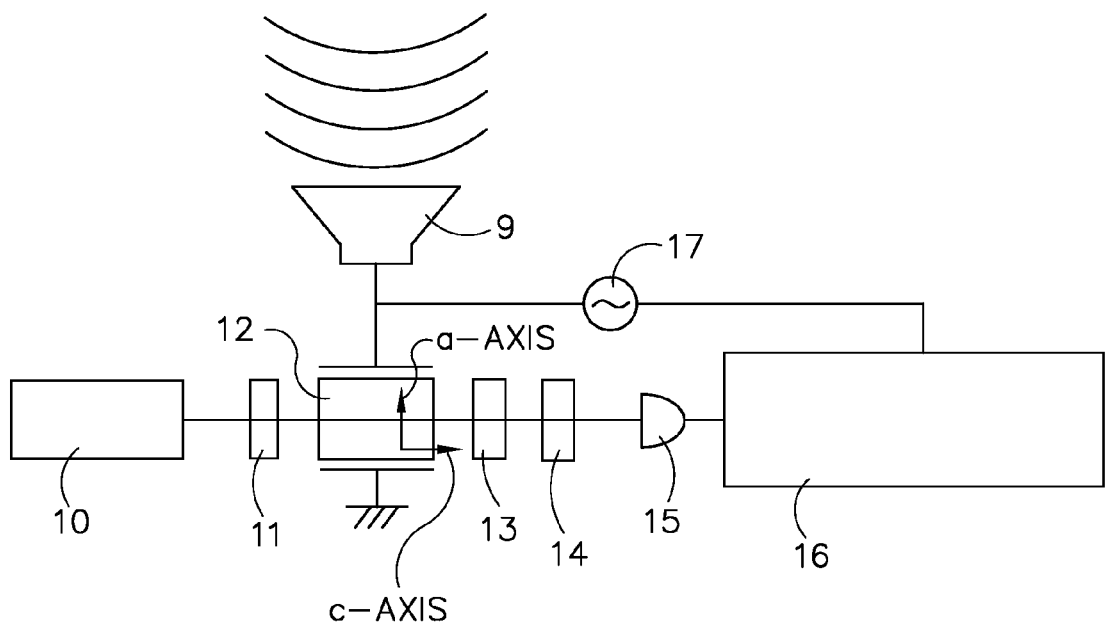
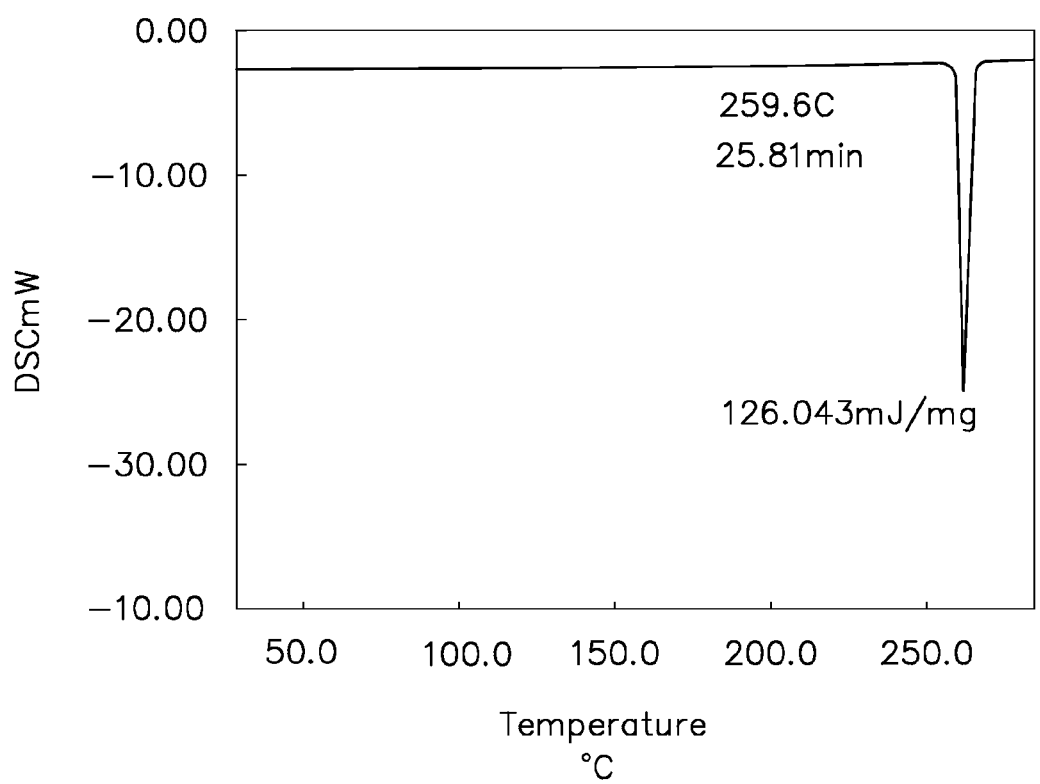
FIG. 6

DAST TWIN CRYSTAL, PROCESS FOR PRODUCING THE SAME, AND USE THEREOF

RELATED APPLICATIONS

This application is a Continuation of PCT/JP2005/000511 filed on 18 Jan. 2005 which claims priority under U.S.C. § 119 to Japanese Patent Application No. 015399/2004 filed 23 Jan. 2004, the entirety of which is incorporated herein by reference.

TECHNICAL FIELD

The present invention relates to a novel 4-dimethylamino-4-stilbazolium tosylate (DAST) twin crystal, a process for producing the same, and a use thereof.

BACKGROUND ART

A DAST crystal has been used as an electro-optic element such as a wavelength conversion device or an electric field sensor because the crystal provides excellent properties as a non-linear optical material. JP 3007972 B. However, the DAST crystal that has been conventionally used as an electro-optic element is a single crystal, and no twin crystal of DAST has been known. A process for producing a DAST crystal was disclosed by Pan et al. Feng Pan, Man Shing Wong, Christian Bosshard, and Peter Guenter, *Adv. Mater.*, 1996, 8, No. 7, 592-595. However, the crystal disclosed by Pan et al. was considered to be defective.

DISCLOSURE OF THE INVENTION

An object of the present invention is to provide a novel DAST twin crystal, a process for producing the DAST twin crystal, and use of the DAST twin crystal.

The inventors of the present invention have prepared a DAST single crystal for many years, and have conducted research on an electro-optic device using the single crystal. Japanese Patent Application No. 2002-247332. As a result of these investigations, they have discovered the inventors of the present invention have found that although it is difficult to obtain a DAST single crystal with a size effective for use as an electro-optic device, a DAST twin crystal can be relatively easily prepared. The advantageous properties of a DAST twin crystal include the following:

1) A DAST twin crystal can be relatively easily prepared as compared to a DAST single crystal, 2) the DAST twin crystal exerts good electro-optical properties as in the case of the DAST single crystal, 3) the DAST twin crystal has such an external appearance that two tabular crystals are joined with each other, so a crystal having wide parallel surfaces and a large effective area can be obtained, and 4) since the two crystals overlap each other, the twin crystal grows faster than the single crystal, and a thick crystal can be easily prepared. The thicker the crystal, the better the sensitivity as an electro-optic element.

The present invention comprises a DAST twin crystal that is relatively easily prepared and useful as an electro-optic device.

Specifically, the present invention comprises the following.

(1) A twin crystal of 4-dimethylamino-4-stilbazolium tosylate (DAST).

(2) A twin crystal according to the above item (1), in which two tabular crystals are joined with each other.

(3) A twin crystal according to the above item (2), in which the two tabular crystals contact with each other while being reversed by 180° C. centering on its a-axis.

(4) A twin crystal according to any one of the above items (1) to (3), further having a thickness of 0.05 to 20 mm.

(5) A twin crystal according to any one of the above items (1) to (4), further having a long side of 0.1 to 100 mm and an aspect ratio of 1 to 20.

(6) A process for producing the 4-dimethylamino-4-stilbazolium tosylate (DAST) twin crystal according to any one of the above items (1) to (5), the process comprising the step of growing a twin crystal from a solution of 4-dimethylamino-4-stilbazolium tosylate (DAST) by using a twin crystal as a seed crystal.

(7) A process for producing the 4-dimethylamino-4-stilbazolium tosylate (DAST) twin crystal according to the above item (6), in which the solution of 4-dimethylamino-4-stilbazolium tosylate (DAST) which has been heated is cooled so that a crystal is precipitated on a porous membrane, and a twin crystal that is precipitated on and remains adhering to the porous membrane is used as the seed crystal.

(8) A process for producing the 4-dimethylamino-4-stilbazolium tosylate (DAST) twin crystal according to the above item (7), comprising using a porous polyfluoroethylene membrane as the porous membrane.

(9) A process for producing the 4-dimethylamino-4-stilbazolium tosylate (DAST) twin crystal described in any one of the above items (1) to (5), further comprising selecting a twin crystal from crystals grown by a slope nucleation method of crystal growth, depending on an external appearance.

(10) An electro-optic device comprising the 4-dimethylamino-4-stilbazolium tosylate (DAST) twin crystal according to any one of the above items (1) to (5).

(11) An electro-optic device comprising a 4-dimethylamino-4-stilbazolium tosylate (DAST) single crystal obtained by removing, e.g., by shaving off or cutting off, one of the crystals of a 4-dimethylamino-4-stilbazolium tosylate (DAST) twin crystal.

(12) An electro-optic device according to the above item (10) or (11), wherein the device is used for an antenna or for detecting an electric field.

According to the present invention, a thick twin crystal can be quickly prepared. The twin crystal according to the invention has good sensitivity when the crystal is used as an electro-optic device.

BRIEF DESCRIPTION OF THE DRAWINGS

[FIG. 5] A device for measuring an electromagnetic wave such as a millimeter-wave by using a DAST twin crystal.

[FIG. 6] A measurement chart of a melting point of a DAST twin crystal by using a differential scanning calorimeter.

DESCRIPTION OF NUMERALS

Figure 1:
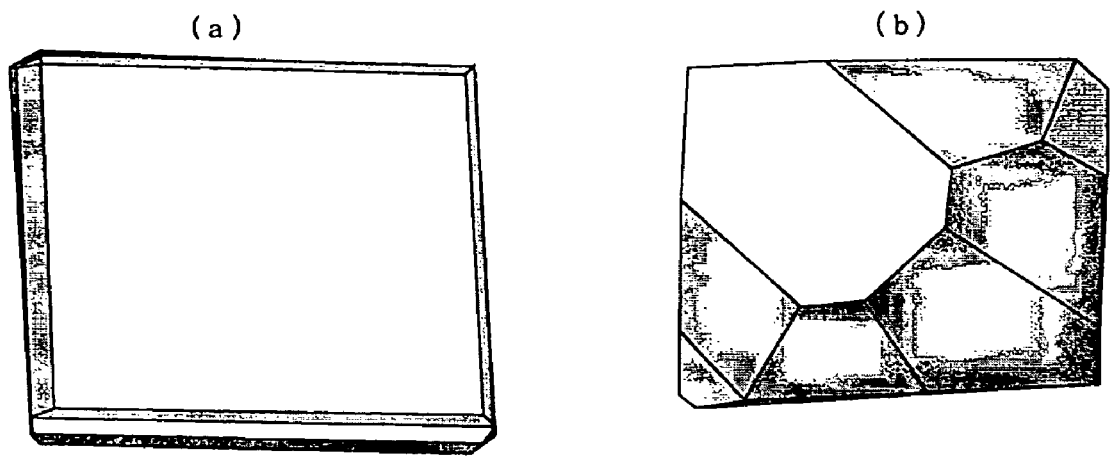
[FIG. 1] An external appearance of a DAST twin crystal (a) and an internal appearance of a DAST single crystal (b).

1: DAST crystal
2: electric wave

3: incident light
4: transmitted light
5: DAST crystal
6: crown glass
7: installation table
8: electrode
9: antenna
10: continuous wave (CW) laser generator
11: polarizer
12: DAST twin crystal
13: phase compensating plate
14: analyzer
15: photodetector
16: electrical measuring instrument
17: local oscillator

BEST MODE FOR CARRYING OUT THE INVENTION

Hereinafter, the present invention will be described in more detail, but the present invention is not limited to the following description.

Process for Producing a DAST Twin Crystal.

Examples of a preferred methods for preparing a DAST twin crystal include a method of using a seed crystal and a slope nucleation method of crystal growth.

Seed Crystal Method

A seed crystal method as a first method is a method of growing a twin crystal from a DAST solution by using a twin crystal as a seed crystal. The inventors of the present invention have made investigation of a process for producing a DAST crystal by the seed crystal method. As a result, they have found that crystals can be efficiently prepared by: cooling a heated DAST solution to precipitate crystals on a porous membrane; and using the crystals precipitated on the porous membrane as a seed crystal in a state that the crystals are adhered to the porous membrane as-is. The DAST crystals precipitated on the porous membrane are classified into a single crystal and a twin crystal depending on their external appearances. When a crystal is grown from the DAST solution using the single crystal selected as a seed crystal, a single crystal can be grown. When a crystal is grown from the DAST solution using the twin crystal selected as a seed crystal, a twin crystal can be grown. Furthermore, the inventors of the present invention have found that polyfluoroethylene is preferably used as a material for the porous membrane in this case.

Specifically, 1 to 10% (w/w), preferably 2 to 3% (w/w), DAST solution is subjected to hot filtration through a filter and added to a bottle having a porous membrane placed on its bottom. Then, the solution is cooled to a temperature lower than the saturation temperature of the solution by 1 to 20° C. DAST synthesized in accordance with a known preparation method described in JP-A-09-512032, JP-A-2001-247400 or the like can be used. Methanol, ethanol, propanol, or the like can be used as the solvent for DAST. Of those, methanol is preferable. Examples of a preferable material for the porous membrane include polyfluoroethylene (Teflon: registered trademark by Du Pont), cellulose, nylon and the like. Of those, polyfluoroethylene is particularly preferable. A desirable pore size is about 0.1 µm to 100 µm, preferably 0.1 µm to 1 µm.

Appropriate stimuli such as opening and closing of a cap of the bottle were applied to the DAST solution in the bottle, whereby nuclei were generated. After that, the solution was left standing for 30 minutes or longer. Then, the porous membrane was taken out. The porous membrane was washed with the solvent having low solubility for DAST (for example, acetone) immediately after taking out, followed by drying. When one in which two crystals do not overlap each other is selected from the crystals on the porous membrane and grown, a single crystal can be obtained. When one in which two crystals overlap each other is selected and grown, a twin crystal can be obtained. The crystals remaining on the porous membrane were carefully observed, and one in a state where two crystals overlapped each other was selected. A portion of the porous membrane to which seed crystals adhered was carefully cut into appropriate shapes for each seed crystal, and was grown in the DAST solution.

Growth was performed under the following conditions. One end of the porous membrane to which seed crystal adhered was fixed in a bottle by appropriate means, and was hung in a DAST solution having a concentration of 1 to 10% (w/w), preferably 4 to 6% (w/w). Methanol, ethanol, propanol, or the like is used as the solvent same as the above-described. Of those, methanol is preferable. After that, the surface of the seed crystal is slightly dissolved at a temperature slightly higher than the saturation temperature (temperature higher than the saturation temperature by 0.1° C. to 5° C.) for 30 seconds to 24 hours, for example, at 45° C. for about 30 minutes. Growth is performed while the solution is left standing without stirring, or is slowly stirred, at a temperature lower than the saturation temperature by 0.1° C. to 10° C. for 5 days to 60 days, for example, at 42 to 43° C. for 2 weeks. Then, the crystal is taken out, whereby a twin crystal is obtained.

Slope Nucleation Method of Crystal Growth

A second method is a production process including selecting a twin crystal from crystals grown by a known slant crystal growing method slope nucleation method of crystal growth (see Patent Document 1) depending on an external appearance. The slope nucleation method of crystal growth as described in Patent Document 1 is suitable for the preparation of a DAST twin crystal because twin crystals are more easily obtained than single crystals.

To be specific, DAST crystals were grown in accordance with the method described in Example of Patent Document 1, and a twin crystal was selected by a method described below.

That is, a DAST powder obtained by a recrystallization method purifying through at least one recrystallization, preferably two or more recrystallization, was added with the solvent, whereby a DAST solution having a concentration of 1 to 10% (w/w) was prepared. Methanol, ethanol, propanol, or the like is used as the solvent. Of those, methanol is particularly preferable. Next, a board made of polyfluoroethylene having at least one groove portion in its main surface (hereinafter referred to as "slope") with an slope angle of 10 to 60° C., preferably 30° C., was immersed in the solution. After that, the DAST powder was completely dissolved by warming the solution. Each of the width and depth of the groove portion is preferably about 0.1 to 1 mm, particularly preferably about 0.5 mm. Then, the solution was cooled down to the temperature of 0.1 to 10° C. lower than the supersaturation temperature of the solution, or was preferably cooled to 42 to 43° C., and the temperature was maintained for 6 hours or longer, preferably 24 hours. Thus, DAST crystals were precipitated in the groove portion. When no crystal was precipitated, the temperature of the solution was lowered (for example, 0.1° C./day) as required to precipitate DAST crystals. After the precipitation of the crystals, the temperature of the solution was maintained or lowered (for example, 0.1° C./day) as required, whereby the crystals was grown to a predetermined size. The DAST crystals was grown in this manner, a DAST twin crystal and a DAST single crystal may be obtained at a ratio of 8:2 to 5:5.

A method of selecting a twin crystal is shown below. In general, a DAST single crystal has one flat plane that the [001] surface expands to almost full size of the crystal. A surface partly parallel to the [001] surface appears on the [00-1] surface side, but the other surfaces have slope surface (regional consortium research and development project in 1998 "Venture company incubation type regional consortium research and development" (core industry creation type) "Consortium research on photonics sensing" outcome report, March, 2000, New Energy and Industrial Technology Development Organization, management corporation "Intelligent Cosmos Research Institute", related organizations Agency of Industrial Science and Technology, the National Institute of Materials and Chemical Research, The Tohoku National Industrial Research Institute). On the other hand, a twin crystal comprises a single parallel plane in which both a [001] surface and a [00-1] surface expand to almost full size of the crystal. A twin crystal can be selected depending on such difference in shape. All of the twin crystals selected in such a manner could be confirmed to be twin crystals by X-ray analysis.

As can be seen from comparison data (Table 1) on a growth rate by the seed crystal method, the growth rate of a twin crystal is higher than that of a single crystal, and the twin crystal is thicker than the single crystal.

a lattice constant were calculated for each group by a basic approach. As a result, unit cells having the same lattice constant and different orientation were assembled in an amount corresponding to two crystals. The fact decided that the measured crystal was a twin crystal.

A relative positional relationship between the two crystals was determined on the basis of the setting parameter and lattice constant thereof. As a result, it was revealed that the crystals were rotated by 180° centering on the a-axis. Lattice constants were 10.33 Å, 11.30 Å, and 17.82 Å, respectively. Those constants coincided with data on a single crystal (10.365 Å, 11.322 Å, and 17.893 Å, respectively, (Feng Pan, Man Shing Wong, Christian Bosshard, and Peter Guenter, *Adv. Mater.*, 1996, 8, No. 7, 592-595).

Properties of Prepared Twin Crystal (Electro-optical Properties.

The electro-optical properties of a DAST twin crystal will be described by using an electric field detector (EO) shown in FIG. 2.

The birefringence of a DAST crystal changes owing to an action of an electric field in a space where the crystal is placed. A change in birefringence is reflected by a change in polarization plane of laser transmitted through the crystal.

Figure 2:
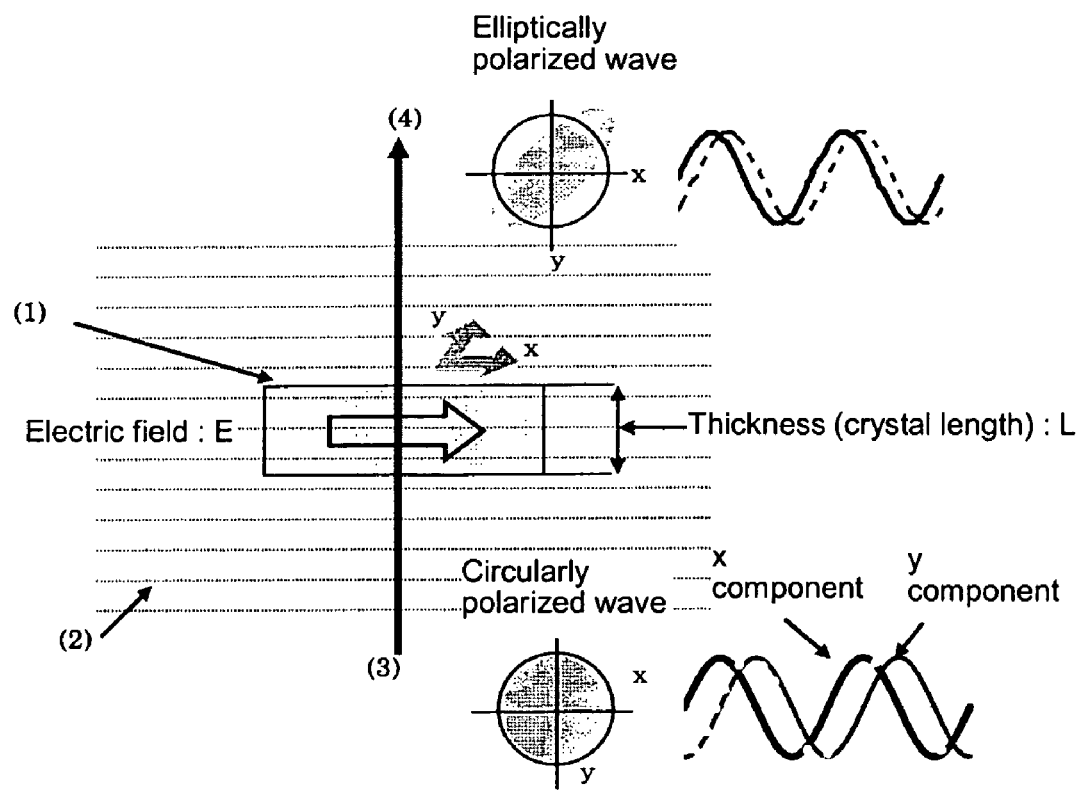
[FIG. 2] A diagram showing that the larger the thickness of a DAST crystal, the higher an EO sensitivity.

In FIG. 2, (1) shows a DAST crystal (electro-optic crystal) placed in an electric field space, and (2) shows that an electric wave is incident in the electric field space.

TABLE 1

| | Grown in the same bottle for 14 days ||||||
| | Single crystal ||| Twin crystal |||
| | Length | Width | Thickness | Length | Width | Thickness |
|---|---|---|---|---|---|---|
| Seed before growth | 1.7 | 1.7 | — | 2.1 | 2.5 | — |
| After growth | 3.0 | 3.2 | 0.38 | 6.0 | 6.1 | 0.86 |
| Difference | 1.3 | 1.5 | — | 3.9 | 3.6 | — |

| | Grown in the same bottle for 15 days ||||||||||||
| | Single crystal ||| Twin crystal ||| Single crystal ||| Twin crystal |||
| | Length | Width | Thickness | Length | Width | Thickness | Length | Width | Thickness | Length | Width | Thickness |
|---|---|---|---|---|---|---|---|---|---|---|---|---|
| Seed before growth | 1.4 | 1.5 | — | 1.4 | 1.5 | — | 1.7 | 1.7 | — | 1.7 | 1.8 | — |
| After growth | 2.7 | 3.0 | 0.42 | 4.3 | 4.8 | 0.76 | 3.1 | 3.4 | 0.41 | 4.0 | 4.8 | 0.84 |
| Difference | 1.3 | 1.5 | — | 2.9 | 3.3 | — | 1.4 | 1.7 | — | 2.3 | 3.0 | — |

Properties of Prepared Twin Crystal (Crystal Properties).

A twin crystal prepared by such a manner as described above has an external appearance as shown in FIG. 1. FIG. 1 shows an external appearance of a twin crystal (a) and an external appearance of a single crystal (b) by comparison. As described above, a DAST single crystal has the [00-1] surface expanding a flat plane and other inclined plane while a DAST twin crystal comprises a single parallel plane expanding to almost full size of the crystal.

The crystal had a long side of 0.1 to 100 mm, a short side of 0.1 to 20 mm, and an aspect ratio of 1 to 20.

X-ray structural analysis was performed by the following approach on the assumption that DAST was a twin crystal. Such high angles (2θ=40° or more) that Diffraction peaks did not overlapped each other to the extent possible were collected, and classified into two groups. A setting parameter and Owing to birefringence, incident light (3) and transmitted light (4) differ from each other in phase shift between the polarized light components of an x-axis direction and a y-axis direction shown in FIG. 2. The shift amount Δθ of the shift is proportional to an electric field intensity E and the thickness (crystal length) L of the crystal.

$$\Delta\theta \propto (n_x^3 r_{11} - n_y^3 r_{21}) EL$$

where $n_x$: refractive index relating the x-axis direction,
$r_{11}$: electro-optic coefficient relating the x-axis direction,
$n_y$: refractive index relating the y-axis direction, and
$r_{21}$: electro-optic coefficient relating the y-axis direction (see, for example, F. Pan, G. Knoepfle, Ch. Bosshard, S. Folloniner, R. Spreiter, M. S. Wong, and P. Guenter, *Appl. phys. Lett.* 1996, 69(1), 13-15).

The intensity of an electric field can be recognized by recording a phase shift amount as a change in intensity by using a polarizer. The larger the thickness (crystal length) L of the crystal, the higher the sensitivity of the crystal. Accordingly, electric field can be detected with higher sensitivity using a DAST twin crystal having a large thickness in comparison with the case using a single crystal.

Figure 3:
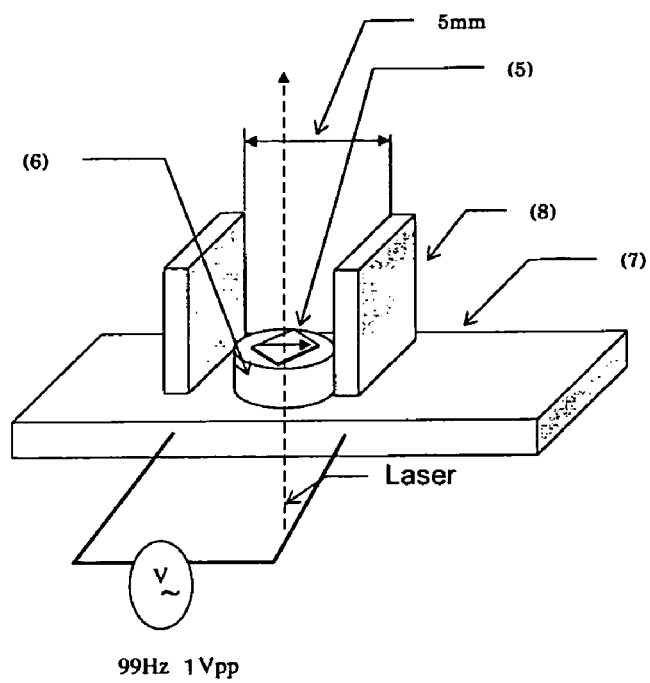
[FIG. 3] An example of a device for measuring an EO sensitivity.

A relationship between an EO sensitivity and a DAST thickness was determined as described below. In FIG. 3, "5" shows a DAST crystal, "6" shows a crown glass on which the crystal is placed, "7" shows an installation table, and "8" shows an electrode. An arrow in the DAST crystal "5" shows an a-axis direction.

An alternating voltage having an amplitude of 1 volt and a frequency of 99 KHz is impressed between the two electrodes "8" provided parallel at a distance of 5 mm, and the DAST crystal "5" is installed in an electric field as shown in FIG. 3. The birefringence of the DAST crystal changes owing to the electric field. Laser having a wavelength of 1.5 μm was transmitted, and a change in polarization of the laser was recorded as a change in intensity by using a polarizer and a photodiode.

Figure 4:
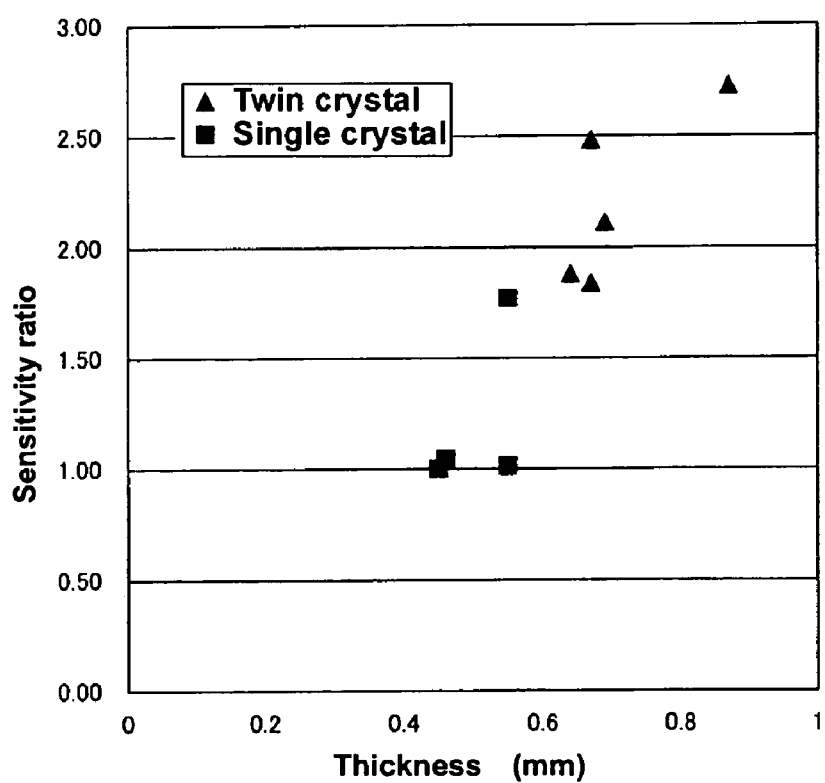
[FIG. 4] A diagram showing a relationship between the thickness of a DAST crystal and an EO sensitivity.

The transmittance of laser changes with crystals. Sensitivities were corrected on the assumption that the intensities of the transmitted laser were same and were plotted versus the thickness of the crystal as shown in FIG. 4. A tendency was clearly observed, in which a sensitivity increased with increasing crystal thickness. In addition, the resultant twin crystal had a larger thickness and a higher sensitivity than those of the resultant single crystal.

The melting point of the DAST twin crystal measured by using a differential scanning calorimeter was 259.6° C. (FIG. 6).

Hereinafter, application examples of a DAST twin crystal will be shown.

A technique referred to as electro-optic sampling (hereinafter abbreviated as EOS) using laser and an electro-optic crystal can be used for detecting an electrical signal or radiated electromagnetic wave in a millimeter wave band. The term "millimeter wave" as used herein it indicates a high-frequency electromagnetic wave covered a wide frequency band ranging from a microwave to a sub-millimeter wave. As described in the documents (Q. Wu et al.: "Free electro-optic sampling of terahertz beams", *Applied Physics Letters, Vol. 67*, 1995, p. 3523-3525, and JP-A-2002-31658), a received high-frequency electrical signal such as a millimeter wave can be detected by converting into a light signal using an electro-optic crystal. The sensitivity of a device can be more increased in the case where a DAST twin crystal which a crystal having an more thick crystal length can be obtained is used than in the case where a DAST single crystal is used.

Description will be given by reference to the device shown in FIG. 5 as an example.

FIG. 5 is a block diagram showing an embodiment of a system that converts an electromagnetic wave such as a millimeter wave into a light signal by using a DAST twin crystal and detects the signal. The system comprises: an antenna "9" for receiving an electromagnetic wave such as a millimeter wave propagating in the space; a continuous wave (CW) laser generator "10"; a polarizer "11" for converting the laser into polarized light; an electro-optic crystal (DAST twin crystal: "12"); a phase compensating plate "13"; an analyzer "14"; a photodetector "15"; an electrical measuring instrument (locking amplifier or spectrum analyzer: "16"; and a local oscillator "17".

A method involving arranging the electro-optic crystal "12" as shown in FIG. 5 to convert a millimeter wave or the like into a light signal can be used for detecting the time waveform of the millimeter wave or the like received from the antenna. A light wave generated from the continuous wave (CW) laser generator "10" is polarized by the polarizer "11", or polarized laser is used. The resultant polarized light is transmitted through the electro-optic crystal "12" arranged in such direction as shown in the figure to enter the photodetector "15" via the phase compensating plate "13" and the analyzer "14". On the other hand, when the amplitude of the received electric wave (frequency ω) is modulated by using the local oscillator "17" (frequency $\omega_{mod}$), a voltage applied to the electro-optic crystal "12" is shown by the following Equation 1.

$$A \frac{1 + \cos\omega_{mod}t}{2} \cos\omega t \qquad \text{Equation 1}$$

The modulated signal from the local oscillator "17" is simultaneously used as a reference signal for the electrical measuring instrument.

When the birefringence $\Gamma_0$ of the electro-optic crystal "12" is compensated by the phase $\Gamma$c of the phase compensating plate "13", and the relationship of $\Gamma_0+\Gamma c=0$ is established, a light-receiving power P in the photodetector "15" is shown by the following Equation 2.

$$P = kR^2L^2A^2\{6 + 8\cos\omega_{mod}t + 2\cos 2\omega_{mod}t + 4\cos(2\omega - \omega_{mod})t + 4\cos(2\omega + \omega_{mod})t + 6\cos 2\omega t + \cos 2(\omega - \omega_{mod})t + \cos 2(\omega + \omega_{mod})t\} \qquad \text{Equation 2}$$

In the equation, L represents a crystal length and A represents the amplitude of an electric wave. This equation shows that the amplitude A of the electric wave can be detected by measuring the component $\omega_{mod}$ or $2\omega_{mod}$ using a lock-in amplifier. Detection capability depends on $R^2L^2$.

R represents a constant related to an electro-optic coefficient, and is a value specific to an electro-optic crystal.

$$R = n_x^3 r_{11} - n_y^3 r_{21}$$

where
- $n_x$: refractive index relating the x-axis direction,
- $r_{11}$: electro-optic coefficient relating the x-axis direction,
- $n_y$: refractive index relating the y-axis direction, and
- $r_{21}$: electro-optic coefficient relating the y-axis direction (see, for example, F. Pan, G. Knoepfle, Ch. Bosshard, S. Folloniner, R. Spreiter, M. S. Wong, and P. Guenter, *Appl. phys. Lett.* 1996, 69(1), 13-15).

In DAST, R is represented as shown below.

$$R = n_x^3 r_{11} - n_y^3 r_{21}: 1160 \text{ pm/V (700 nm)}$$

Therefore, it can be found that performance proportional to the square of the thickness L can be obtained.

Hereinafter, the present invention will be described in more detail by way of examples. However, the present invention is not limited by these examples at all.

EXAMPLE 1

Twin Crystal Production Example 1 (Seed Crystal Method)

2.6% (w/w) DAST solution in methanol was subjected to hot filtration and added to a bottle having a porous polyfluoroethylene membrane (filter material with a pore size of 0.5 μm, PTFE manufactured by ADVANTEC) placed on its bottom. Then, the solution was cooled to 23° C. A stimulus was applied to the solution by opening or closing a cap, whereby a nuclei were generated. 24 hours after that, the membrane was taken out. The membrane was washed with acetone and ethyl acetate immediately after taking out, followed by drying. The crystals remaining on the porous membrane were carefully observed, and crystals being in a state where two crystals overlapped each other were selected. Each portion of the membrane to which seed crystals adhered was carefully cut out into a strap shape containing seed crystal, and each seed crystal was grown in the DAST solution.

Growth was performed under the following conditions.

A membrane to which a seed crystal having a shape in which two crystals overlapped each other adhered was selected. The membrane was fixed its end to a mesh made of polyfluoroethylene by a fishing gut, and was hung in 4.6% (w/w) DAST solution of in methanol. After that, the surface of the seed crystal was slightly dissolved at 46° C., which is a temperature slightly higher than the saturation temperature, for 20 minutes, then at 45° C. for 30 minutes, and then at 44° C. for 10 minutes. Growth was performed in accordance with a temperature drop method while the solution was slowly stirred by a stirrer. The solution was cooled from 43.4° C. to 42.5° C. at 0.1° C./12 hours, and then at 0.1° C./24 hours. 15 days after that, a crystal was taken out.

The resultant crystal had a long side of 4.8 mm, a short side of 4.0 to 4.3 mm, and a thickness of 0.76 to 0.84 mm.

EXAMPLE 2

Twin Crystal Production Example 2 (Slope Nucleation Method of Crystal Growth)

DAST crystals were grown in accordance with the method described in Example of JP 3007972 B (Patent Document 1), and a twin crystal was selected by a method as described below.

That is, 7.0 g of DAST powder purified by twice recrystallization were added with 200 mL of methanol, whereby the DAST solution was prepared. Next, a board made of polyfluoroethylene having 10 grooves having a width of 0.5 mm and a depth of 0.5 mm in its main surface was immersed in the solution at an inclination angle of 30° C. After that, the solution was warmed, and the DAST powder was completely dissolved. Then, the solution was cooled to 42.5° C., and the temperature was maintained for 24 hours. Thus, DAST crystals were precipitated in the grooves. After the precipitation of the crystals, the solution was cooled (for example, at 0.1° C./day), whereby the crystals were grown. The DAST crystals was able to be prepared by the ratio of 6 (DAST twin crystal):4 (DAST single crystal) by growing the DAST crystals in said manner.

Parallel plate type crystals were selected, and the X-ray analysis of the crystals confirmed that all of them were twin crystals. The resultant crystals had a long side of 2.8 to 6.2 mm, a short side of 2.0 to 5.8 mm, a thickness of 0.44 to 0.76 mm, and an aspect ratio of 5.4 to 8.6.

EXAMPLE 3

An example for performing the reception of a millimeter wave or the like by using a DAST twin crystal will be shown.

By referring to FIG. 5, a system was built-up, which converts an electromagnetic wave such as a millimeter wave into a light signal by using a DAST twin crystal and detects the signal. The system comprises: an antenna "9" for receiving an electromagnetic wave such as a millimeter wave propagating in the space; a continuous wave (CW) laser generator "10"; a polarizer "11" for converting the laser into polarized light; a DAST twin crystal "12"; a phase compensating plate "13"; an analyzer "14"; a photodetector "15"; an electrical measuring instrument (locking amplifier or spectrum analyzer: "16"); and a local oscillator "17".

A light wave generated from the continuous wave (CW) laser generator "10" is polarized by the polarizer "11", and the polarized light is then transmitted through the DAST twin crystal "12" arranged in such direction as shown in the figure to enter the photodetector "15" via the phase compensating plate "13" and the analyzer "14". On the other hand, when the amplitude of the received electric wave (frequency $\omega$) is modulated by using the local oscillator "17" (frequency $\omega_{mod}$), a voltage applied to the DAST twin crystal "12" is as shown by the following Equation 3.

$$A\frac{1+\cos\omega_{mod}t}{2}\cos\omega t \qquad \text{Equation 3}$$

The modulated signal from the local oscillator "17" is simultaneously used as a reference signal for the electrical measuring instrument.

When the birefringence $\Gamma_0$ of the DAST twin crystal "12" is compensated by the phase $\Gamma c$ of the phase compensating plate "13" and the relationship of $\Gamma_0+\Gamma c=0$ is established, a light-receiving power P in the photodetector "15" is shown by the following Equation 4.

$$P=kR^2L^2A^2\{6+8\cos\omega_{mod}t+2\cos 2\omega_{mod}t+4\cos(2\omega-\omega_{mod})t+4\cos(2\omega+\omega_{mod})t+6\cos 2\omega t+\cos 2(\omega-\omega_{mod})t+\cos 2(\omega+\omega_{mod})t\} \qquad \text{Equation 4}$$

In the equation, L represents a crystal length and A represents the amplitude of an electric wave. This equation shows that the amplitude A of the electric wave can be detected by measuring the component $\omega_{mod}$ or $2\omega_{mod}$ using a lock-in amplifier.

EXAMPLE 4

An example of X-ray structural analysis will be shown.

A twin crystal was identified and analyzed as described below.

(1) Peak search: Scanning was performed on a certain angle range (2θ=40° C. to 50° C.) to search fifty diffraction intensity peaks.

(2) Attribution of diffraction peaks: A setting parameter was determined from the fifty diffraction intensity peaks, and reflection indices were calculated from the setting parameter and the coordinates of (1). As a result, two groups were classified, that is, in one group all of h, k, and l became an integer and in the other group only h did not become an integer.

(3) Assembly of primitive lattice: A setting parameter and a lattice constant were determined for each of the two groups. As a result, unit cells having the same lattice and different orientation were assembled in an amount corresponding to two crystals. It was revealed that the analyzed crystal was a twin crystal.

(4) Analysis of relative positional relationship between two crystals: Though the crystal had been treated as a primitive lattice of triclinic crystal in the operations (1) to (3), the crystal was converted into a monoclinic C base-centered lattice having higher symmetry in order to analyze a relative positional relationship. Reciprocal lattice vectors were plotted on the basis of each lattice constant and each setting parameter when reflection indices were (1, 0, 0), (0, 1, 0), and (0, 0, 1). Then, a relative positional relationship between two unit lattices in a reciprocal lattice space was determined. The relationship was converted from a reciprocal lattice to a real lattice. As a result, it was revealed that each crystal was rotated by 180° C. centering on its a-axis.

The DAST twin crystal and process for producing the same of the present invention, can be used to produce an electro-optic device having a high sensitivity.

The invention claimed is:

1. A process for producing a 4-N,N-dimethylamino-N-methyl-4'-stilbazolium tosylate (DAST) twin crystal comprising the step of growing a twin crystal from a solution of 4-N,N-dimethylamino-N-methyl-4'-stilbazolium tosylate 4-(DAST) by using a twin crystal as a seed crystal.

2. The process for producing the 4-N,N-dimethylamino-N-methyl-4'-stilbazolium tosylate (DAST) twin crystal according to claim 1, wherein the solution of 4-N,N-dimethylamino-N-methyl-4'-stilbazolium tosylate (DAST) which has been heated is cooled so that a crystal is precipitated on a porous membrane, and a twin crystal that is precipitated on and remains adhering to the porous membrane is used as the seed crystal.

3. The process for producing the 4-N,N-dimethylamino-N-methyl-4'-stilbazolium tosylate (DAST) twin crystal according to claim 2, comprising using a porous polyfluoroethylene membrane as the porous membrane.

4. A process for producing a 4-N,N-dimethylamino-N-methyl-4'-stilbazolium tosylate (DAST) twin crystal comprising selecting a twin crystal from crystals grown by a slope nucleation method of crystal growth, depending on an external appearance.

5. An electro-optic device comprising a 4-N,N-dimethylamino-N-methyl-4'-stilbazolium tosylate (DAST) twin crystal.

6. A process for producing an electro-optic device comprising:

removing one crystal of a 4-N,N-dimethylamino-N-methyl-4'-stilbazolium tosylate (DAST) twin crystal to form a 4-N,N-dimethylamino-N-methyl-4'-stilbazolium tosylate (DAST) single crystal; and forming an electro-optic device comprising the 4-N,N-dimethylamino-N-methyl-4'-stilbazolium tosylate (DAST) single crystal.

7. The process for producing an electro-optic device according to claim 6, wherein the device functions as an antenna or for detecting an electric field.

8. The process for producing an electro-optic device according to claim 6 further comprising:

growing a 4-N,N-dimethylamino-N-methyl-4'-stilbazolium tosylate (DAST) twin crystal from a solution of 4-N,N-dimethylamino-N-methyl-4'-stilbazolium tosylate (DAST) by using a twin crystal as a seed crystal.

* * * * *